(12) United States Patent
Perricone

(10) Patent No.: US 6,743,433 B2
(45) Date of Patent: Jun. 1, 2004

(54) TREATMENT OF ACNE USING ALKANOLAMINE COMPOSITIONS

(76) Inventor: Nicholas V. Perricone, 27 Coginchaug Ct., Guilford, CT (US) 06437

( * ) Notice: Subject to any disclaimer, the term of this patent is extended or adjusted under 35 U.S.C. 154(b) by 0 days.

(21) Appl. No.: 10/085,864

(22) Filed: Feb. 27, 2002

(65) Prior Publication Data

US 2003/0021855 A1 Jan. 30, 2003

Related U.S. Application Data

(63) Continuation-in-part of application No. 09/900,680, filed on Jul. 6, 2001, now abandoned.

(51) Int. Cl.[7] .......................... A61K 7/48; A61K 7/40; A61K 7/50; A61P 17/10; A61P 17/00
(52) U.S. Cl. ...................... 424/401; 424/63; 424/62; 514/859; 514/448; 514/724; 514/725; 514/458; 514/440; 514/561; 514/667
(58) Field of Search ........................ 424/401, 63, 62; 514/859, 448, 724, 725, 458, 440, 561, 667

(56) References Cited

U.S. PATENT DOCUMENTS

| | | |
|---|---|---|
| 4,710,489 A | 12/1987 | Meister et al. |
| 5,541,162 A | 7/1996 | Ohmori et al. |
| 5,554,647 A | 9/1996 | Perricone |
| 5,646,190 A | 7/1997 | Martin |
| 5,965,618 A | 10/1999 | Perricone |
| 6,319,942 B1 | 11/2001 | Perricone |
| 6,365,623 B1 | 4/2002 | Perricone |

FOREIGN PATENT DOCUMENTS

WO    WO 95/05852    3/1995

OTHER PUBLICATIONS

Brogden, R.N., and Goa, K.L., Drugs 63: 1–12 (1997).
Downie, M.T., and Kealey, T., J. Invest Derm. 111: 199–205 (1998).
Ibbotson, S.J., J. Invest. Derm., 112: 933–938 (1999).
Physicians' Desk Reference 2002, 56th ed., 2522–2524.

*Primary Examiner*—Frederick Krass
*Assistant Examiner*—Clinton Ostrup
(74) *Attorney, Agent, or Firm*—St. Onge Steward Johnston & Reens LLC

(57) ABSTRACT

Acne is treated or prevented by the topical application of compositions containing an alkanolamine such as dimethylaminoethanol, tyrosine, and a sulfur ingredient such as lipoic acid or glutathione. Adjunct ingredients such as fatty acid esters of ascorbic acid, e.g., ascorbyl palmitate and α-hydroxy acids may be included in the formulations. Compositions of the invention may be used alone, or, in many preferable embodiments, in combination with conventional acne medications such as anti-acne products containing salicylic acid, benzoyl peroxide, or a retinoid. In these embodiments, alkanolamine compositions of the invention are applied to affected skin areas first, and then a conventional acne medication is applied. This maximizes the efficacy of the treatment while minimizing skin irritation caused by conventional medications.

4 Claims, No Drawings

TREATMENT OF ACNE USING ALKANOLAMINE COMPOSITIONS

CROSS-REFERENCES TO RELATED APPLICATIONS

This is a continuation-in-part of co-pending U.S. patent application Ser. No. 09/900,680, filed Jul. 6, 2001 abandoned.

BACKGROUND OF THE INVENTION

1. Field of the Invention

This invention relates to improved compositions and methods for the treatment and prevention of acne, and the promotion of clear skin.

2. Description of Related Art

This invention relates primarily to methods and compositions for the treatment of acne vulgaris. Acne is the most common pustular condition of the skin, disfiguring afflicted persons with inflammatory and noninflammatory lesions (including pustules, papules and comedones) during the active phase, and with atrophic scars afterwards. It occurs most commonly in teenagers, but is not confined to adolescents, as increasing numbers of persons aged >20 years are seeking advice on treatment for acne (Brogden, R. N., and Goa, K. L., *Drugs*, 1997, 53: 511–519; this reference and others cited below are hereby incorporated herein in their entireties by reference). Although acne is generally considered to be self-limiting, its social effects can be substantial, and it may have its most severe effects on the psyche (ibid.). In about 60% of teenagers, disease severity and embarrassment are sufficient for them to self-medicate with proprietary preparations and/or seek medical advice.

Acne is a multifactorial disease affecting the pilosebaceous units of the skin. Each unit consists of a large, multilobed sebaceous gland, a rudimentary hair and a wide follicular canal lined with stratefied squamous epithelium. They are found over most of the body surface but are largest and most numerous on the face, chest, and upper back. Normally, desquamated follicular cells are carried to the surface by the flow of sebum. Under the abnormal circumstances of acne vulgaris, an abnormal desquamation process provokes increased sloughing of the epithelium, which becomes more cohesive because of defective keratinization. This process causes blockage of the follicular orifice with accumulation of dead cells. Androgen stimulates the undifferentiated hormonally responsive cells making up the outer layer of the sebaceous gland lobule to divide and differentiate. Sebum production favors proliferation of the anaerobe *Propionibacterium acnes*, which is a normal commensal to the pilosebaceous unit, which can elicit hypersensitivity responses in acne.

The basic lesion of acne is the microcomedo. Accumulation of sebum and keratinous debris results in a visible closed comedo, or whitehead, and its continued distension causes an open comedo, or blackhead. The dark color of blackheads is due to oxidized melanin. Blackheads and microcysts are noninflammatory lesions of acne, but some comedones evolve into inflammatory papules, pustules, or nodules, and can become chronic granulomatous lesions. The initial inflammatory cell in an acute acne papule is the CD4+T lumphocyte. Duct rupture is not a prerequisite for inflammation, which is due to the release of pro-inflammatory substances from the duct. When inflammation develops, neutrophil chemotaxis occurs. These neutrophils secrete hydrolytic enzymes that cause further damage and increased permeability of the follicular wall. In pustules, neutrophils are present much earlier. More persistent lesions exhibit granulomatous histology that can lead to scarring.

The aims of treating acne are to minimize the number and severity of lesions, prevent scarring, limit disease duration, and reduce the social and psychological stress that affects many patients, particularly teenagers. Conventional treatment is directed at correcting the three major factors that seem to cause acne: (1) androgenic stimulation of the sebaceous glands and increased sebum production; (2) abnormal keratinization and impaction in the pilosebaceous canal causing obstruction to sebum flow; and (3) proliferation of P. acnes. Thus, topical agents that remove comedones, such as topical retinoids are particularly effective because they normalize desquamation within the follicular orifice, which allows the sebum to flow freely onto the surface of the skin; adalpalene, tretinoin, and tazarotene have been shown to have efficacy in treating mild to moderate acne, but all three have reported to have skin-irritating side effects including erythema, pruritis, burning/stinging, and scaling/flaking (*Physicians' Desk Reference®*, 56th ed. 2002, p. 2523, hereinafter referred to as "PDR"). The side effects of retinoid use are so extreme that many individuals cannot tolerate topical application of these agents at all.

Salicylic acid and benzoyl peroxide have been used to treat acne for some time. Both agents dry the skin, which helps in acne management, but they cause some skin irritation in perilesional skin areas of acne patients, especially patients with sensitive skin, and in some cases the erythema is extreme. Moreover, it has been recently reported that benzoyl peroxide seems to induce free radical production that can produce skin changes that qualitatively resemble ultraviolet B damage, e.g., increases in epidermal thickness, and deleterious changes in elastin and glycosaminoglycan content (Ibbotson, S. H., et al., *J. Inves. Derm.*, 1999, 112: 933–938). Topical and oral antibiotics (especially tetracycline, erythromycin, and clindamycin) are sometimes prescribed for patients with inflammatory papules and pustules, but, in addition to the undesirability of antibiotic overuse in general, which can lead to enhanced susceptibility to infection, disadvantages to such treatments include phototoxicity and interactions with other medications. Other factors that play a role in exacerbating acne, including oil-based cosmetics and some drugs (e.g., androgenic hormones, high-progestin birth control pills, systemic corticosteroids, and iodide- and bromide-containing agents) are often minimized during acne treatment.

Human sebum contains an unusual mixture of lipids, with the major lipid classes being triacylglycerides (TAG, conventional fat, ≈40 to 60%), wax esters (≈19 to 26%), and squalene (≈11 to 15%), but at least 15 different neutral and polar lipids have been identified in human sebaceous gland tissue (Downie, M. M. T., and Kealey, T., *J. Invest. Denn.*, 1998, 111: 199–205). Recent studies have shown that people with acne have abnormal sebum secretions in that the ratios of essential fatty acids in sebaceous triacylglycerides (TAG, conventional fat) are skewed, as are the proportions of TAG, squalene and wax esters. It has been hypothesized that the viscosity and irritant level of these substances contribute to sebum obstruction and rupture of pilosebaceous units observed in acne. Lipogenesis in human sebaceous glands varies depending upon the metabolic state of the cells, glandular fluctuations, and the presence or absence of different substrates or other substances effecting competitition between sterol and TAG pathways (Downie and Kealey, cited above). It would be desirable to utilize this biochemical information to devise alternate treatments for acne.

It would be desirable to treat and prevent acne vulgaris manifested by the symptoms of pustule, papule, and comedone formation described above, minimizing the number and severity of lesions. It would also be desirable to provide a homogeneous skin complexion, while simultaneously reducing pore size, evening out skin texture, minimizing scar formation, treating acneform scars left after resolution of the active phase, promoting clear and firm skin tone, and providing a healthier look. It would also be desirable to have topical compositions that are effective in ameliorating skin irritation caused by conventional acne formulations so that more efficacious therapies can be devised for individuial patients based on their different medical needs, including therapies that combine different treatments.

BRIEF SUMMARY OF THE INVENTION

It is an objective of this invention to provide improved compositions and methods for the treatment of acne vulgaris, both during the active phase, and for acneform scars afterwards, and for the prevention of acne and pore size reduction. It is another objective of the invention to provide acne compositions and ingredients for compositions that can be used in combination with conventional acne medications to reduce inflammation and redness, and methods for using compositions of the invention with conventional acne treatments to provide new combination therapies that maximize acne management. It is a corresponding objective to alleviate the negative social and psychological impacts frequently suffered by persons afflicted with acne. Facial lesions and scars are one of the strongest forces driving the cosmetic industry. It would be desirable to have new and improved methods for treating acne, as it is so widely observed in the population, particularly among teenagers who are especially sensitive about their appearance and embarrassed with acne lesions and their disfiguring scars.

It is a more specific objective of the invention to provide topical compositions and methods for acne lesion and acne scar treatment as well as acne prevention, including the visible reduction of skin pores, based upon the application of compositions containing dimethylaminoethanol and/or other structurally related alkanolamines, in combination with tyrosine and sulfur or a sulfur-containing active ingredient such as lipoic acid, glutathione, and/or sulfur resorcinol. Many preferred compositions further employ other adjunct ingredients, including, but not limited to, α-hydroxy acids such as glycolic and/or lactic acid, and fatty acid esters of ascorbic acid such as ascorbyl palmitate. Adjunct ingredients enhance the efficacy of the treatment, and help to minimize or eliminate skin irritation to perilesional areas.

Compositions of the invention may be formulated with effective amounts of other active ingredients found in conventional acne medications, e.g., salicylic acid, retinoids such as tretinoin, adapalene, or tazarotene, or benzoyl peroxide. More preferably, compositions of the invention are used in combination with conventional medications, in therapies that involve sequential application of at least two compositions, a conventional medication and a composition of the invention, to offset the toxic effects of commercial products while simulataneously enhancing the overall efficacy of the acne therapy by providing multiple active ingredients that act synergistically to produce maximal anti-acne benefits. This embodiment takes advantage of the dual anti-acne and anti-inflammatory properties observed with the use of alkanolamine compositions of the invention.

BRIEF DESCRIPTION OF THE INVENTION

This invention is based upon the finding that alkanolamines are efficacious in the treatment of acne, reducing acne papules, providing clearer skin, and inducing skin firming and a healthier look, and upon the development of alkanolamine compositions containing other active ingredients that provide a superior acne therapy, alone, or in combination with conventional acne treatments.

As used herein, the term "acne" includes all types of acne involving the skin and its oil glands and hair follicles in all stages, including acne vulgaris observed in adolescents, acne observed in endocrinologic conditions characterized by excess androgen secretion, and the like, in the active inflammatory (pustule-, papule-, comedone-forming) and noninflammatory (blackhead- and cyst-forming) phases, and postinflammatory (healing, scarring, and scarred) phase. By "reducing redness and inflammation" is meant visibly reducing apparent erythema in the skin. In typical embodiments, erythema is visibly reduced in both the acne lesions and in perilesion areas surrounding microcomedos. Improved acne products and therapies of the invention visibly decrease the number of blackheads, whiteheads, pimples, and blemishes, decrease the severity of lesions and shorten their healing time, and minimize or eliminate erythema.

"Conventional acne medications" encompasses previously described compositions containing effective amounts of active anti-acne ingredients. The term includes, but is not limited to, the over-the-counter acne drug products set out in 21 C.F.R. § 333.310 for the management and treatment of acne, namely sulfur, resorcinol, resorcinol monoacetate, combinations of sulfur and resorcinol, and salicylic acid, as well as readily available commercial products that contain benzoyl peroxide as an active ingredient. "Conventional acne medications" also include previously described anti-acne compositions that contain effective amounts of comedolytic and keratolytic agents and/or compounds that dry the skin and absorb sebum generally available without a prescription including, but not limited to, other peroxides such as lauroyl peroxide or carbamide peroxide, ethanol, phenoxy ethanol, propanol, phenoxy propanol, ethyl acetate, azelaic acid, fumic acid, dehydroacetic acid, pyruvic acid, urea, cetyl betaine, scymnol sulfate, cholate, deoxycholate, flavinoids, and soaps and natural plant extracts that diminish the oily/shiny appearance of skin. "Conventional acne medications" further include those typically available with a prescription, including anti-acne compositions containing effective amounts of retinoids or antibiotics. Adalpalene, tretinoin, and tazarotene are retinoids that have been used in conventional acne medications. Antibiotics used in anti-acne medications administered orally or topically, typically the latter, include effective amounts of erythromycin, antibiotics of the lincomycin family, particularly lincomycin and clindamycin, and antibiotics of the tetracycline family, particularly tetracycline, doxyclycline, meclocycline, and minocycline.

In the practice of the invention, compositions containing an effective amount of an alkanolamine of the formula

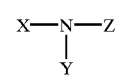

wherein X, Y and Z are selected from the group consisting of hydrogen, $C_1$–$C_3$ alkyl groups, $C_2$–$C_4$ alkanol group, wherein at least one of X, Y, or Z is a $C_2$–$C_4$ alkanol group bearing at least one hydroxyl group and optionally at least one carboxyl group, are applied to skin areas affected by acne or susceptible to acne. Useful compounds for the invention include, but are not limited to, ethylaminoethanol, methylaminoethanol, dimethylaminoethanol, isopropanolamine, triethanolamine, isopropanoldimethylamine, ethylethanolamine, 2-butanolamine, choline, serine, and mixtures thereof. Many preferred embodiments employ methylaminoaminoethanol, dimethylaminoethanol, ethylaminoethanol, and/or triethanolamine; particularly preferred is dimethylaminoethanol (DMAE).

The amount of alkanolamine necessary to treat acne is not fixed per se, and necessarily is dependent upon the identity of alkanolamine employed, the amount and type of other active and adjunct ingredients employed, the user's skin type, and the severity and extent of the acne and/or acneiform scars. Most compositions of the invention contain from about 0.1% to about 10% by weight, more narrowly from about 0.25% to about 5% to 7% by weight, and in many cases from about 1% to about 3% by weight, alkanolamine such as dimethylaminoethanol in the total composition, typically in association with a dermatologically acceptable carrier more fully described below. In the examples that follow, efficacious compositions illustrating the invention contain 2 to 3% DMAE.

DMAE and/or other structurally related alkanolamines are applied in compositions that contain tyrosine and a sulfur ingredient. Alkanolamine compositions of the invention typically contain from about 0.01% to about 6%, more narrowly from about 0.03% to about 5% by weight, and, in many embodiments, from about 0.2% to about 0.5% by weight tyrosine, based on the total composition. Compositions illustrated in the examples that follow contain from 0.1 to 0.5% tyrosine.

The sulfur ingredient includes, but is not limited to, sulfur, sulfacetamide, a combination of sulfur and resorcinol (often called "sulfur resorcinol" in the literature), a combination of sulfur and resorcinol monoacetate, lipoic acid, glutathione, and their biologically active derivatives. Sulfur ingredients are typically present in the alkanolamine compositions of the invention in amounts ranging from about 0.1% to 0.5% up to 15%, more narrowly from about 0.5% to 10% by weight. Sulfur (5%) and sodium sulfacetamide (10%) are active ingredients marketed as a Plexion™ suspension. Where sulfur and resorcinol or sulfur and resorcinol monoacetate are all are part of the sulfur ingredient, typical concentrations range from about 3% to about 8 to 10% by weight of the composition.

Lipoic acid is the sulfur ingredient used in some embodiments illustrated hereafter. The term "lipoic acid" encompasses thioctic acid (1,2-dithiolane-3-pen-tanoic acid; 1,2-dithiolane-3-valeric acid), $C_8H_{14}O_2S_2$, formula weight 206.32, and its reduced form, dihydrolipoic acid. It has been variously known as acetate replacing factor, protogen A, and pyruvate oxidation factor. As used herein, where the properties and advantages of "lipoic acid" (or LA) are discussed as an active ingredient in the practice of the invention, both lipoic acid and its derivatives are encompassed. "Lipoic acid derivatives" include thioctic acid esters, particularly alkyl esters such as fatty acid esters, amides, particularly those isolated from or mimicking naturally occurring lipoamides, salts, particularly alkali metal salts, anhydrides and specifically includes the reduced form, dihydrolipoic acid and its esters, amides and salts. One particularly efficacious derivative that exhibits increased cellular uptake and biological activity useful in the practice of the invention is N,N-dimethyl,N-2-amidoethyl lipoate recently described by Sen, C. K., et al. (*Free Radical Biol. Med.*, 1998, 25: 89) and called lipoic acid plus (LA-Plus). Derivatives may also include those involving other reactive groups known to those skilled in the art. As used herein, the term "derivatives" includes metabolic precursors of lipoic acid. Where lipoic acid derivatives are employed, they must be functionally equivalent to lipoic acid.

Since lipoic acid is both fat- and water-soluble, it is an advantage of the invention that, where employed, lipoic acid can be used as an active ingredient in either lipid or aqueous-based compositions, and it readily crosses cellular membranes and disperses in extracellular and intracellular tissue components. It is another advantage of the invention that lipoic acid has been used previously for the treatment of scars (U.S. Pat. No. 5,965,618 to Perricione), including atrophic acneform scars, and for the treatment of acne (U.S. patent application Ser. No. 09/475,514, filed Dec. 30, 1999 and allowed on Dec. 21, 2001). Employing it with alkanolamines and other active ingredients significantly improves the effect. Lipoic acid-containing formulations typically contain from about 0.1% to about 7% by weight lipoic acid. Many embodiments contain more than 1 weight % lipoic acid, e.g., from about 1.1% to about 3 to 5% by weight lipoic acid. One efificacious embodiment contains from about 2% to about 3% lipoic acid by weight.

Another sulfur ingredient useful in alkanolamine compositions and illustrated hereafter is glutathione. The term "glutathione" encompasses the tripeptide N-(N-L-γ-glutamyl-L-cysteinyl)glycine, often called L-glutathione, glutathione-SH, or γ-Glu-Cys-Gly, and sold under a variety of tradenames such as Agifutol S™, Copren™, Deltathione™, Isethion™, Neuthion™, Tathiclon™, Tathion™ and Triptide™. An advantage of this embodiment of the invention is that glutathione, the major low molecular weight thiol in living plant or animal cells, is readily available and known to be safe when applied topically. As used herein, where the properties and advantages of "glutathione" (or GSH) are discussed as an active ingredient in the practice of the invention, biologically active glutathione derivatives are encompassed. "Glutathione derivatives" include, but are not limited to, reduced glutathione (or GSSG), glutathione salts, particularly reduced glutathione potassium or sodium salts, and glutathione alkyl esters, particularly $C_1$ to $C_{10}$ alkyl esters, especially monoesters such as monomethyl and monoethyl esters which have the glycine carboxylic acid grou acylated, as these have been shown to increase cellular levels of glutathione (U.S. Pat. No. 4,710,489 to Meister), and corresponding amides and imides (such as those set out in U.S. Pat. No. 5,541,162 to Ohmori, et al. Where employed, glutathione-containing compositions of the invention contain from about 0.5% to about 15%, more narrowly from about 5% to about 10% by weight, and even more narrowly from about 8% to about 10% by weight glutathione.

Compositions of the invention may be formulated to contain other anti-acne active ingredients used in conventional acne medications including, but not limited to, peroxides such as benzoyl peroxide, lauroyl peroxide, and carbamide peroxide; alcohols such as ethanol, phenoxy ethanol, propanol, phenoxy propanol, resorcinol; other compounds known to dry skin such as ethyl acetate; acids such as salicylic acid, azelaic acid, fumic acid, dehydroacetic acid, and pyruvic acid; urea and/or cetyl betaine; scymnol sulfate; cholate and/or deoxycholate; retinoids such as adalpalene, tretinoin, and tazarotene; antibiotics such as erythromycin, lincomycin, clindamycin, tetracycline and meclocycline; and the others previously mentioned, and mixtures of any of these. As summarized above, using other anti-acne active ingredients in combination with alkanolamine active ingredients improves the overall therapy in many cases. Conventional anti-acne active ingredients are added to alkanolamine compositions in effective amounts such as those found in commercial products; example ranges are set out below with their descriptions. However, many formulations containing other active ingredients in alkanolamine compositions have a short shelf life. Therefore, preferred methods of the invention which incorporate conventional acne medications are those in which the alkanolamine composition is applied topically to affected skin areas before or after topical application of a commercial acne product. In preferred embodiments, the alkanolamine composition is applied before applying the conventional acne medication. Further details about this embodiment are given below.

Some alkanolamine compositions of the invention contain at least one adjunct ingredient in addition to active ingredients. Adjunct ingredients include, but are not limited to, α-hydroxy acids, fatty acid esters of ascorbic acid, and vitamin A and vitamin A derivatives. Many embodiments employ more than one adjunct ingredient. Where employed, adjunct ingredients have additive effects if not synergistic effects due to different mechanisms of action.

As used herein, the term "α-hydroxy acid" has reference to and encompasses the general class of organic compounds containing at least one hydroxy group and at least one carboxyl group, and wherein at least one hydroxyl group is located on the α-carbon atom. Typically, the compounds are organic acids having at least one carboxylic acid group and at least one hydroxyl group on the α-carbon atom, and may contain other functional groups including additional hydroxyl and carboxylic acid moieties. Preferred α-hydroxy acids and/or α-hydroxy acid derivatives are less bulky structurally so that they penetrate the skin well, and thus have a backbone of from one to three carbon atoms such as those more fully described by Applicant in U.S. Pat. No. 5,965,618 to Perricone at column 6 lines 4 to 29. Where employed, glycolic and/or lactic acid or their derivatives are preferred; glycolic acid is especially efficacious. Glycolic acid or other α-hydroxy acids are typically present in amounts ranging from about 1% to about 10%, more narrowly from about 3% to about 7% of the total composition.

Fat-soluble fatty acid esters of ascorbic acid (vitamin C) is employed as an adjunct ingredient in other embodiments, alone or in combination with α-hydroxy acids. The more oxidation-resistant saturated fatty acid esters of ascorbic acid are preferred, including, but not limited to, ascorbyl laurate, ascorbyl myristate, ascorbyl palmitate, ascorbyl stearate, and ascorbyl behenate. Ascorbyl palmitate is used in one embodiment. As denoted herein, where fatty acid esters are described, e.g., ascorbyl stearate, compositions having predominantly that ester, e.g., predominantly stearate, are included. The esters may be prepared using hydrogenated oils or fats, or fractions thereof, and contain small amounts of another ester. Ascorbyl stearate prepared using canola, for example, commonly contain about 4% ascorbyl palmitate. It is an advantage of the invention that where fatty acid esters of ascorbic acid are employed as an adjunct ingredient, they help stabilize the alkanolamine in the composition. Ascorbyl palmitate and the like ascorbyl esters are typically present in amounts ranging from about 0.5% to about 15%, preferably from about 1% to about 7% to 10%, of the total composition. Vitamin A or vitamin A derivatives may be alternative or additional adjunct ingredients in like concentrations. Vitamin A and vitamin A derivates include, but are not limited to, retinol, retinyl palmitate, retinoic acid, retinal, and retinyl propionate.

Only effective amounts of alkanolamine compositions are needed to treat or prevent acne and minimize erythema when used alone, or in combination with other acne medications more fully discussed below, so generally topical application is accomplished in association with a carrier, and particularly one in which the alkanolamine active ingredient is soluble per se or is effectively solubilized (e.g., as an emulsion or microemulsion). Where employed, the carrier is inert in the sense of not bringing about a deactivation or oxidation of the active ingredient(s), and in the sense of not bringing about any adverse effect on the skin areas to which it is applied. In one preferred practice of the invention, the active ingredients are applied in admixture with a dermatologically acceptable carrier or vehicle (e.g., as a lotion, cream, ointment, soap, stick, or the like) so as to facilitate topical application and, in some cases, provide additional therapeutic effects as might be brought about, e.g., by moisturizing of the affected skin areas. While the carrier for dermatological compositions can consist of a relatively simple solvent or dispersant such as water, it is generally preferred that the carrier comprise a composition more conducive to topical application, and particularly one which will form a film or layer on the skin to which it is applied so as to localize the application and provide some resistance to washing off by immersion in water or by perspiration and/or aid in the percutaneous delivery of the active agent(s). Many preparations are known in the art, and include lotions containing oils and/or alcohols and emollients vegetable oils, hydrocarbon oils and waxes, silicone oils, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophilic colloids. One preferred embodiment is a solution used to saturate a pad used to wipe affected areas; another is a cleanser; and others are lotions, creams, and gels. Such compositions are referred to herein as dermally or dermatologically acceptable carriers, and are formulated using conventional techniques known to those of ordinary skill in the art.

Suitable carriers include water, alcohols, oils and the like, chosen for their ability to dissolve or disperse active ingredients. Generally, even low concentrations of active ingredients in a carrier are suitable, depending upon the application regimen and the active and adjunct ingredients employed. Mild acne typically requires lower concentrations of active ingredients than to acute conditions such as that sometimes observed in adolescence. As a practical matter, however, to avoid the need for repeated application, it is desirable that the topically applied composition be formulated to contain the amounts of active ingredients set out above. Generally in the practice of methods of the invention, the composition is topically applied to the affected skin areas as needed to lesions, often as a tinted cover-up, or at predetermined intervals as a cleanser or a lotion, cream, or gel, it generally being the case that gradual improvement is noted with each successive application. Insofar as has been determined based upon clinical studies to date, no adverse side effects are encountered. It is an advantage of the invention that compositions of the invention do not require a pharmaceutical prescription.

Topical compositions of the invention can comprise additional ingredients commonly found in skin care compositions and cosmetics, such as, for example, tinting agents, tinting agents, emollients, skin conditioning agents, emulsifying agents, humectants, preservatives, antioxidants, perfumes, chelating agents, etc., provided that they are physically and chemically compatible with other components of the composition. Preservatives include, but are not limited to, $C_1$–$C_3$ alkyl parabens and phenoxyenthanol, typically present in an amount ranging from about 0.5% to about 2.0% by weight percent, based on the total composition. Emollients, typically present in amounts ranging from about 0.01% to 5% of the total composition include, but are not limited to, fatty esters, fatty alcohols, mineral oils, polyether siloxane copolymers, and mixtures thereof. Humectants, typically present in amounts ranging from about 0.1% to about 5% by weight of the total composition include, but are not limited to, polyhydric alcohols such as glycerol, polyalkylene glycols (e.g., butylene glycol, propylene glycol, dipropylene glycol, polypropylene glycol, and polyethylene glycol) and derivatives thereof, alkylene polyols and their derivatives, sorbitol, hydroxy sorbitol, hexylene glycol, 1,3-dibutylene glycol, 1,2,6-hexanetriol, ethoxylated glycerol, propoxylated glycerol, and mixtures thereof. Emulsifiers, typically present in amounts from about 1% to about 10% by weight of the composition, include, but are not limited to, stearic acid, cetyl alcohol, stearyl alcohol, steareth 2, steareth 20, acrylates/$C_{10\text{-}30}$ alkyl acrylate crosspolymers, and mixtures thereof. Chelating agents, typically present in amounts ranging from about 0.01% to about 2% by weight, include, but are not limited to, ethylenediamine tetraacetic acid (EDTA) and derivatives and salts thereof, dihydroxyethyl glycine, tartaric acid, and mixtures thereof. Antioxidants, typically present in an amount ranging from about 0.02% to about 0.5% by weight of the composition, include, but are not limited to, butylated hydroxy toluene (BHT); vitamin C and/or vitamin C derivatives, such as fatty acid esters of ascorbic acid, particularly asocorbyl palmitate; butylated hydroanisole (BHA); phenyl-α-naphthylamine; hydroquinone; propyl gallate; nordihydro-quiaretic acid; vitamin E and/or derivatives of vitamin E, including tocotrienol and/or tocotrienol derivatives; calcium pantothenates; green tea extracts; mixed polyphenols; and mixtures of any of these. As mentioned above, particularly preferred antioxidants are those that provide additional benefits to the skin such as ascorbyl palmitate. (See additional ingredients and methods in U.S. Pat. Nos. 4,775,530, 5,376,361, 5,409,693, 5,545,398, 5,574,063, 5,643,586, 5,709,868, 5,879,690, 5,965,618, 5,968,618, 6,051,244, 6,162,419, and 6,191,121 to Perricone).

Buffering agents are employed in many compositions. Preferably, the amount of buffering agent is one that results in compositions having a pH ranging from about 4.5 to about 8.5, more preferably from about 5.5 to about 8.5, most preferably from about 6.5 to about 8.0. Typical buffering agents are chemically and physically stable agents commonly found in cosmetics, and can include compounds that are also adjunct ingredients such as citric acid, malic acid, and glycolic acid buffers.

As summarized above, alkanolamine compositions of the invention may be applied before or after application of a conventional acne medication available over-the-counter or by prescription. These methods are particularly efficacious in therapies for moderate to severe acne and advantageously combine the anti-inflammatory and anti-acne properties of alkanolamine compositions of the invention, and take advantage of the comedolytic, keratolytic, and drying properties of other anti-acne ingredients previously described, while minimizing the redness and inflammation often caused by when these products are applied to skin, especially sensitive skin. Many conventional acne medications contain 0.5% to 2% salicylic acid or 3% to 10% benzoyl peroxide, marketed as Aveeno®, Benvoxyl®, Biore®, Clean and Clear®, Clinac™, Clearasil®, ClearLogix®, Fostex®, Oxy Balance®, PanOxy®, SalAc®, Stridex®, Triz®, and ZapZit® products sold as gels, creams, lotions, astringents, bars, and cleansers. A 20% azelaic acid cream is sold under the name Finevin™.

Alkanolamine compositions of the invention are especially useful when used before or after topical application of a composition containing at least one retinoid. Useful retenoids include commercially available adapalene, tazarotene and/or tretinoin. Adapalene, for example, is sold as a gel or solution marketed as Differin®. Tretinoin can be obtained as a cream, gel or encapsulated microsphere marketed as Avita®, Renova®, Retin-A®, or Retin-A®Micro®. Tazarotene is marketed as a Tazorac® gel. Effective formulations typically contain from about 0.025% to about 0.1% by weight retinoid or retinoid mixture. It is an advantage of the invention that use of alkanolamine compositions with retinoid compositions methods for treating acne that can employ less retinoid than would be required if a retinoid is used alone, further minimizing skin irritation observed in some patients. It is unfortunate that many acne patients in their zeal to rid themselves of blemishes and pimples tend to overuse the medications. Using compositions of the invention can reduce this amount and the duration of drug use in patients presenting acne conditions warranting the beneficial normalizing desquaminating properties that retinoids can provide, and alleviate side effects. Compositions of the invention also minimize or eliminate skin irritation, particularly in areas surrounding acne lesions, while at the same time treating acne lesions.

Alkanolamine compositions may also be used in combination with topical antibiotics such as tetracycline, clindamycin, and erythromycin sometimes used for acne cases, particularly for patients with inflammatory papules and pustules. Clindamycin, for example, is sold in a gel, lotion, solution, marketed as BenzaClin™, Cleocin®, Clindagel™, and Clindets® (which also contains 5% benzoyl peroxide). Erythromycin is sold in a gel marketed as Emgel®. Doxycycline is a tetracycline marketed as a Vibramycin® monohydrate suspension; another tetracycline, minocycline, is also marketed as a Minocin® suspension. Topical antibiotics typically contain from about 0.05% to 0.5% to about 2% active ingredient; formulations containing 1% antibiotic are common. As with retinoid therapy, an advantage of using alkanolamine compositions with antibiotics in cases where the latter are indicated is that a lower antibiotic dose or a shorter antibiotic regimen may be employed. As has been mentioned, it is now recognized that prevalent use of antibiotics in general is undesirable, and long-term use of antibiotics can cause enhanced susceptibility to infection, nausea, gastrointestinal upset, phototoxicity, and interactions with other medications. Use of alkanolamines advantageously augments the treatment and minimizes the amount of antibiotic necessary to cause improvement in patients presenting with an extreme inflammatory phase of acne, and helps to minimize or eliminate side effects.

In therapies that combine topical application of compositions of the invention and topical application of conventional acne medications, alkanolamine compositions are preferably applied first, followed by application of a commercial product. This prevents erythema caused by the product. Saturated pads were used for this purpose in examples that follow; alkanolamine compositions were wiped on affected skin areas, which were then treated with a gel or cream containing a retinoid, a peroxide, or an antibiotic. However, as set out above, any other topical administration may be used. In alternate embodiments, alkanolamine compositions are administered after treatment with a conventional medication or during treatment. Best results are obtained if the two compositions are applied immediately before or immediately after one another, but the invention encompasses embodiments involving a lag period between dosings.

It is an advantage of the invention that topical application of an alkanolamine composition of the invention containing about 2% to about 3% by weight DMAE, for example, typically results in a decrease in redness within an hour of topical application. Beneficial effects are immediate, and formulations of the invention are well-tolerated by the skin. It is another advantage of the invention already discussed that alkanolamines are anti-inflammatories, and decrease erythema in both lesions and perilesional areas. Since compositions of the invention are both anti-inflammatory and anti-acne, their use in combination with conventional acne medications, particularly those requiring a prescription, reduce the need for frequent application of these products and high concentrations of irritating ingredients in these products. Use of combination treatments provides superior acne therapies.

It is a further advantage of the invention that topical administration of alkanolamine compositions provide other beneficial alkanolamine effects: alkanolamines advantageously treat and prevent skin damage and aging (U.S. Pat. No. 5,554,647 to Perricone), increase subcutaneous muscle tone (ibid.), prevent and treat acne scars (U.S. Pat. No. 5,965,618 to Perricone) and disfigurement, and cause visible contraction of skin pores (U.S. patent application Ser. No. 09/900,680, filed Jul. 6, 2001), resulting in clearer, smoother appearing complexion, firmer skin tone, and a healthier look. The results are cumulative. With continued applications, skin tone increases and pores become smaller and tighter over time, enhancing the appearance of skin areas not affected by acne and decreasing the number of clogged pores that cause acne whiteheads.

EXAMPLES

The following examples are presented to further illustrate and explain the present invention and should not be taken as limiting in any regard. Unless otherwise indicated, all percentages are by weight of the total composition.

Example 1

This example describes clinical trials illustrating the efficacy of using compositions and methods of the invention for the treatment of acne.

A cream composition containing 2% dimethylaminoethanol, 0.5% tyrosine, 2% lipoic acid, and 2% glycolic acid was applied to affected skin areas of acne patients twice daily during an eight-week trial. Both inflammatory and noninflammatory lesions were signficantly diminished.

A cover-up composition containing 3% dimethylaminoethanol, 0.5% tyrosine, and 10% glutathione in a tinted base was applied as needed to inflammatory papules and nodules in skin areas affected by acne. Not only was a reduction in the severity of the lesions observed, but also there was an observable decrease in the length of lesion healing time during the duration of a two-week trial. Another successful cover-up composition contained 2% dimethylaminoethanol, 2% lipoic acid, 10% glutathione, and 0.2% tyrosine in a similar study; it was noted by the patients that this composition was especially efficacious in drying the lesions.

A cleanser composition containing 2% dimethylaminoethanol, 0.2% tyrosine, and 0.2% lipoic acid was tested by washing affected skin areas of acne patients twice daily with the formulation. The patients showed improvement over the four weeks of the test. Improvement was also observed in patients washing with a cleanser containing 0.5% ascorbyl palmitate and the same amounts of DMAE, tyrosine, and LA.

A pad saturated with a solution containing 3% dimethylaminoethanol, 0.5% tyrosine, 1% salicylic acid, and 0.1% lipoic acid was used as a face wipe twice daily on affected skin areas of acne patients. Improvement was observed during the course of the several week trial.

Example 2

This example illustrates the efficacy of using compositions of the invention with conventional acne treatments to reduce skin irritation observed with conventional treatments and to maximize the therapy.

In one trial, affected skin areas of acne patients were wiped with a pad saturated with a solution containing 3% dimethylaminoethanol, 0.5% tyrosine, and 2% lipoic acid. Afterwards, a commercial 2% benzoyl peroxide gel product was applied to the same areas following instructions on the product's label. Less skin irritation was observed with this sequential treatment than that observed when the same patients used the benzoyl peroxide gel alone on another day. The same results were obtained when pads saturated with the same composition containing DMAE, tyrosine, and LA were used as a wipe before applying a commercial 2% salicylic acid acne treatment composition. Significantly less skin irritation was observed when the therapy involved pretreatment with compositions of the invention.

Another trial compared skin irritation observed when a commercial Retin-A® was used on acne lesions and irritation observed when skin areas were treated with compositions of the invention beforehand. In this test, patients wiped affected skin areas with pads saturated with 3% dimethylaminoethanol, 0.2% tyrosine, and 2% lipoic acid and then applied 0.1% Retin-A®. Pretreatment according to the invention resulted in significantly less skin irritation than that observed when tretenoin alone was applied, and patients who could not tolerate Retin-A® could use it if they wiped their acne with pads of the invention before applying tretenoin. Moreover, acne skin regions on all patients using the combination therapy was considerably improved over regions treated with the Retin-A® product alone.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for treating acne comprising
   A) first applying to affected skin areas a composition comprising
      1) an effective amount of an alkanolamine selected from the group consisting of ethylamino-ethanol, methylaminoethanol, dimethylaminoethanol, isopropanolamine, triethanolamine, isopropanoldimethylamine, ethylethanolamine, 2-butanolamine, choline, serine, and mixtures thereof;
      2) tyrosine; and
      3) an effective amount of a sulfur ingredient selected from the group consisting of liquid acid, glutathione, sulfur, a combination of sulfur and resorcinol, a combination of sulfur and resorcinol monoacetate, sulfacetamide, and mixtures thereof; and
   B) then applying to the same areas a composition comprising an effective amount of a conventional acne medication containing an active anti-acne ingredient selected from the group consisting of benzoyl peroxide, lauroyl peroxide, carbamide peroxide, ethanol, phenoxy ethanol, propanol, phenoxy propanol, resorcinol, ethyl acetate, salicylic acid, azelaic acid, fumic acid, dehydroacetie acid, pyruvic acid, urea, cetyl betaine, scymnol sulfate, chocolate, deoxycholate, adalpalene, tretinoin, tazarotene, erythromycin, lincomycin, clindamycin, tetracycline and meclocycline.

2. A method according to claim 1 wherein the alkanolamine is dimethylamino-ethanol; the sulfur ingredient is lipoic acid, glutathione or a mixture thereof; and the conventional acne medication is benzoyl peroxide, salicylic acid, or tretinoin.

3. A method according to claim 2 wherein the composition contains from about 0.03% to about 0.5% by weight dimethylaminoethanol, from about 0.03% to about 5% by weight tyrosine, and from about 1% to about 10% by weight lipoic acid, glutathione, or a mixture of lipoic acid and glutathione.

4. A method according to claim 3 wherein the alkanolamine is applied by a pad and the conventional medication as a cream or gel.

* * * * *